Oct. 8, 1974 E. W. LOWDEN Plant Pat. 3,634
RASPBERRY PLANT
Filed Aug. 29. 1973
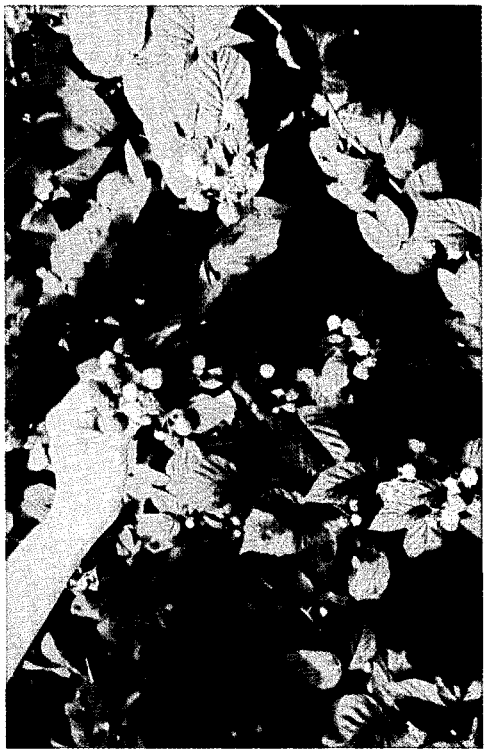
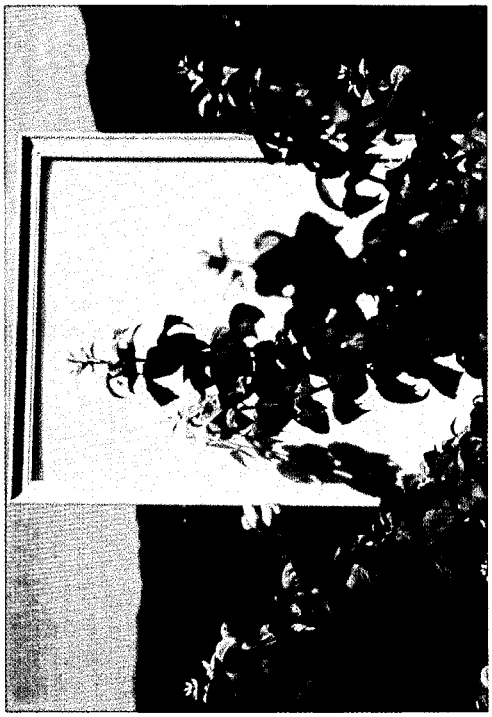
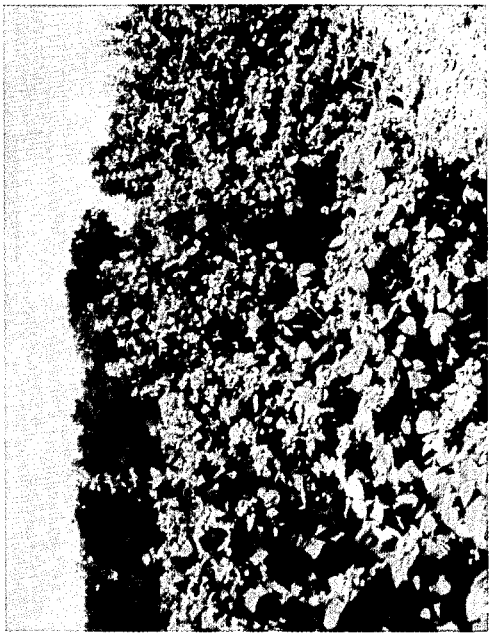

United States Patent Office

Plant Pat. 3,634
Patented Oct. 8, 1974

3,634
RASPBERRY PLANT

Edward W. Lowden, P.O. Box 10,
Ancaster, Ontario, Canada

Filed Aug. 29, 1973, Ser. No. 392,799
Int. Cl. A01h 5/03
U.S. Cl. Plt.—46 1 Claim The present invention relates to a new and distinct variety of sweet purple raspberry plant which was selected by me from a block of seedlings which I derived from crossing the raspberry variety known as "Lowden's Black" (U.S. Pat. No. 2,013) with a very late-ripening, unnamed and unpatented black raspberry chance seedling which came up in one of my cold frames during experimental breeding work conducted by me for many years on my property located at Ancaster, Ontario, Canada.

As the result of this breeding, I have produced a new and improved raspberry vaiety which is definitely different from any other of the many varieties which have become known to me during my long experience of over 50 years in the growing and breeding of various raspberry varieties. My new sweet purple raspberry variety is endowed with important and commercially valuable features which constitute a unique combination in the class of purple raspberries, as evidenced by the following principal characteristics which are outstanding therein:

(1) Stout, very strong and very upright canes which have an extensive but compact branching habit in a spiral arrangement;
(2) Complete feedom from the production of suckers;
(3) An unusual and very noticeable restriction and cupping of the leaves for a considerable distance down from the tips of the canes when leafing out in the spring and which persists for a substantiail period of time thereafter during the growing season;
(4) A complete absence of thorns on the leaves, and fewer and blunter shorter thorns than normal on the canes, with the latter having a purplish tint;
(5) Exceptionally good immunity to virus and anthracnose infections;
(6) A relatively late berry ripening habit;
(7) Medium size berries which have exceptionally small seeds and which are borne in clusters of medium to large size;
(8) A less acid and sweeter berry flavor than the berries of most other purple raspberries; and
(9) A green berry color until the berries near maturity, then turning bright red which soon darkens to light purple and finally becomes dark purple before the berries become over-ripe.

Asexual reproduction of my new raspberry variety by tip-layering, as performed by me on my cultivated property at Ancaster, Ontario, Canada, shows that the foregoing characteristics and distinctions come true to form and are established and transmitted though succeeding propagations.

The accompanying drawing shows a typical block of field plants of my new raspberry variety, as well as a close-up view depicting their unusual cupped, young tip-leaf growth, and a close-up view of typical berry clusters, with the berries being in different color stages, all as depicted in color as nearly true as it is reasonably possible to make the same in a composite color illustration of this character.

The following is a detailed description of my new raspberry variety, as based on observations made at Ancaster, Ontario, Canada, with color terminology in accordance with Koster's Color Guide, except where general color terms of ordinary dictionary signficance are obvious:

Parentage: A selected seedling derived from a cross of "Lowden's Black" with an unnamed chance seedling.

Propagation: Holds its distingiushing characteristics through succeeding propagations by tip-layering.

Dates of first and last pickings: From about 5 to 7 days later than "Lowden's Black," but more variable; can also be picked and used during red berry color stage contrary to other purple varieties; very much later than the early crops of "Purple Autumn Sodus," "Burgundy" (U.S. Plant Pat. No. 1,567), "Columbian" and later than "Clyde," all unpatented except "Burgundy"; it is one of the latest of all raspberry vaieties grown in the region of Ontario, Canada.

Plant:

*Growth*—Very vigorous on sand, but medium on heavier soil; not as tall as "Purple Autumn."

*Root*—Medium vigorous.

*Leaves*—Many; medium size; leaves develop late; no thorns on leaves; leaves are noticeably and distinctly restricted and cupped for a considerable distance down from the tips of the canes when leafing out in the spring and continue so for a substantial period of time thereafter during the growing season.

*Canes*—Very upright; attain height of about 7 feet, with extensive but compact branching which occurs in a spiral arrangement; shot thorns on canes which have a purplish tint.

Bloom: *Late.*

*Size*—Medium.

Fruiting stems: Long; slim.

Fruit: Borne in medium to large clusters; extremely free of crumbling.

*Length*—About ⅝ inch.

*Width*—About ¾ inch.

*Color*—Near Yellowish Green, Plate 73, at first until near maturity, becoming bright red or near Carmine, Plate 29, and then gradually darkening to light purple or near Bright Violet, Plate 61, and finally becoming a Dark Purple color, near Plate 56.

*Flesh*—Much less juicy than "Lowden's Black" or perhaps any other purple variety.

*Flavor*—Less acid and sweeter than most other purple raspberries; more closely resembles flavor of red raspberries.

*Seeds*—Exceptionally small and perhaps the smallest of any known raspberry seed.

Soil where grown: Grows well on sand and silt loam with fair drainage.

Culture: Mineral cultivation required and no spraying whatsoever needed.

Drought resistance: Good.

Disease resistance: Excellent resistance to virus and anthracnose infections, as determined from prolonged observations over period of some 15 years during which my new variety remained clean and healthy without any sign of infection, while other raspberry vaieties grown in close proximity thereto under the same conditions at Ancaster, Ontario, Canada, were heavily infected.

Use: Market; local; dessert; especially suitable for freezing and canning.

I claim:

1. A new and distinct variety of sweet purple raspberry plant, substantially as herein shown and described, characterized particuarly as to novelty by the unique combination of stout, very strong and very upright canes which have an extensive but compact habit in a spiral arrangement, complete freedom from the production of suckers, an unusual and very noticeable restriction and cupping of the leaves for a considerable distance down from the tips of the canes when leafing out in the spring and which persists for a substantial period of time thereafter during the growing season, a complete absence of thorns on the leaves, and fewer and blunter shorter thorns than normal on the canes, with the latter having a purplish tint, exceptionally good immunity to virus and anthacnose infections, a relatively late berry ripening habit, medium size berries which have exceptionally small seeds and which are borne in clusters of medium to large size; a less acid and sweeter berry flavor than the berries of most other purple raspberries, and a green berry color until the berries near maturity, then turning bright red which soon darkens to light purple and finally becomes dark purple before the berries become ove-ripe.

No references cited.

ROBERT E. BAGWILL, Examiner